United States Patent [19]
Till

[11] Patent Number: 5,833,763
[45] Date of Patent: Nov. 10, 1998

[54] PROCESS FOR CLEANING CONTAINERS

[75] Inventor: Volker Till, Hofheim am Taunus, Germany

[73] Assignee: GEA Till GmbH & Co., Kriftel, Germany

[21] Appl. No.: 716,057

[22] Filed: Sep. 19, 1996

[30] Foreign Application Priority Data

Sep. 22, 1995 [EP] European Pat. Off. ............... 95114919

[51] Int. Cl.⁶ ................ B08B 7/04; B08B 3/00; B08B 3/04; B08B 3/12
[52] U.S. Cl. .............. 134/18; 134/82; 134/83; 134/104.1; 134/105; 134/165; 134/184
[58] Field of Search .......... 134/82, 83, 104.1, 134/105, 165, 184, 18

[56] References Cited

U.S. PATENT DOCUMENTS 4,170,241  10/1979  Clapp ........................................ 134/83

FOREIGN PATENT DOCUMENTS

| 27 38 571    | 5/1978 | Germany . |
| 40 25 624 A1 | 2/1991 | Germany . |
| 42 34 466 A1 | 4/1994 | Germany . |
| Wo 9406357   | 4/1994 | WIPO .    |

Primary Examiner—Ardin H. Marschel
Assistant Examiner—Jezia Riley
Attorney, Agent, or Firm—Alix, Yale & Ristas, LLP

[57] ABSTRACT

A method of cleaning a reusable container includes the steps of (1) pre-rinsing the container with a pre-rinse fluid; (2) chemically cleaning the container; (3) post-rinsing the container with a post-rinse fluid; (4) introducing a contaminate indicator into the container prior to the step of post-rinsing; and (5) testing the post-rinse fluid for the presence of the contaminate indicator during at least a portion of the post-rinsing step. A number of alternative embodiments employ various contaminate indicators which may be introduced into the container at various points during the cleaning process.

10 Claims, No Drawings

PROCESS FOR CLEANING CONTAINERS

BACKGROUND OF THE INVENTION

1. Field of the Invention

The present invention relates to the field of reusable fluid containers of the type in which beverages are transported from a producer to consumers. More particularly, the present invention concerns multi-step processes for cleaning reusable fluid containers of the type which include a pre-rinse step, a chemical cleaning step, and a post-rinse step. Accordingly, the general objects of the present invention are to provide novel and improved methods and apparatus of such character.

2. Description of the Related Art

Reusable containers have been widely used to transport fluid products from producers to consumers for many years. Such reusable containers are intended to retain a fluid product prior to usage by a consumer and, after being consumed, returned to the original producer for subsequent cleaning and refilling. The use of reusable containers is particularly wide-spread in the consumer beverage industry. For example, reusable beer bottles and/or kegs and the like are quite commonly delivered to taverns and, after subsequent consumption of the beverage contained therein, returned to the brewery for reuse. Upon return of the beer containers to the brewery, the containers are cleaned prior to refilling thereof. Traditionally, this cleaning process entailed (1) emptying any product residue remaining in the container; (2) pre-rinsing the container with water; (3) chemically cleaning the container; (4) rinsing the container with water to remove any chemical residues which may remain after the chemical cleaning step; and (5) sterilizing the newly cleaned container by subjecting it to sterilizing steam. Once this cleaning process has been completed, the newly cleaned and sterilized containers can then be refilled with a beverage, sealed and redelivered to the tavern for consumption of the refilling beverage. Naturally, this cycle can be repeated a number of times.

In order to preserve the integrity of the refilling beverage, it is imperative that all living organisms be removed from a reusable container prior to refilling the container with the beverage. Restated, the presence of any microorganisms in the refilled container will allow the microorganisms to feed on the beverage and reproduce, thereby damaging the quality of the beverage in the container.

One possible source of such microorganisms is the beverage itself. That is, microorganisms can potentially enter a refilled beverage container along with the refilling beverage. Since a properly pasteurized beverage should be bacteria-free, however, this potential source of contamination rarely contaminates a refilled container in practice.

Another potential, and much more likely, source of such contaminating microorganisms is an improperly cleaned reusable container. Often, any living microorganism which may be present within the container throughout the cleaning process can be killed using saturated steam to sterilized the container just prior to refilling. However, malfunctions sometimes occur in the cleaning and/or sterilization machinery which can result in one or more of the cleaning steps being improperly performed or even entirely omitted. When such malfunctioning goes undetected, bacteria can survive the improper cleaning and/or sterilization processes and contaminate a refilled container. Even if the malfunction is not serious enough to cause immediate beverage damage, deposits can accumulate in the container, over the course of several refilling cycles, thereby making further cleanings more difficult. For example, if only steam sterilization is performed during several cleanings, a sponge-like layer of contaminants can build up over repeated usage cycles of the container. While this build-up may be effectively steam sterilized if the container has only been refilled a few times, the build-up will eventually accumulate to the point where proper sterilization can no longer occur. When this happens, bacteria located within a central core of the build-up are protected from the high cleaning temperatures reached during sterilization. This protection is provided by a sponge-like arrangement of pores and bubbles in the build-up which form an insulation layer around the bacteria hidden therein. Thus, even after proper cleaning procedures are performed on such a container, the protected microorganisms can survive the cleaning process and contaminate the beverage once the container has been refilled.

In order to ensure that the refilled beverage containers delivered to the consumer are not contaminated by microorganisms as described above, it is presently customary to periodically sample refilled beverage containers for contamination prior to delivery to a customer. These beverage samples are typically taken from randomly selected refilled containers and incubated in culture dishes of a laboratory over the course of several days. The incubated product samples are then analyzed to determine the extent to which cell colonies have developed, if at all, during laboratory incubation. Based on this analysis, conclusions can be reached regarding the quality of the beverage producer's container cleaning and sterilization machinery and/or beverage pasteurization processes.

While the above-described testing process can effectively determine whether a given batch of refilled beverage containers has been contaminated, this process requires at least several days to produce usable test results. In the interim, production must continue on the assumption that no contamination problems exist. If a contamination problem does arise, several days of production will have been at least partially contaminated and, therefore, must be discarded.

Therefore, there exists a need in the art for novel and improved methods and apparatus for cleaning reusable containers and for quickly and accurately determining the effectiveness of such cleaning.

SUMMARY OF THE INVENTION

It is, accordingly, one object of the present invention to provide a method of cleaning reusable containers which also allows simultaneous monitoring of the effectiveness of the cleaning process.

It is another object of the present invention to provide a method of cleaning reusable containers which allows more rapid detection and removal of contaminated reusable beverage containers.

It is yet another object of the present invention to increase the quality of beverages contained in reusable containers.

These and other objects and advantages are provided by the present invention by providing a method of cleaning a reusable container which includes the steps of (1) pre-rinsing the container with a pre-rinse fluid; (2) chemically cleaning the container; (3) post-rinsing the container with a post-rinse fluid; (4) introducing a contaminate indicator into the container prior to the step of post-rinsing; and (5) testing the post-rinse fluid for the presence of the contaminate indicator during at least a portion of the step of post-rinsing.

A wide variety of contaminate indicators may be utilized with the present invention and the indicator may be introduced into the container at any point in the cleaning process prior to the step of post-rinsing. Among the preferred indicators are those which have the ability to adhere to surface irregularities presented by contaminate deposits or cracks in the containers, but do not adhere to smooth metal, glass and/or plastic walls of the container. Using such indicators, it is possible to detect the presence of contaminate deposits and/or container cracks based on the presence or absence of the indicator during the post-rinse phase of the cleaning process. For example, if no cracks and/or contaminate deposits exist in the container, any indicator introduced into the container will be flushed out early in the post-rinse phase. Thus, at the end of the post-rinse step, little or no indicator will be detected in the post-rinse fluid. This failure to detect the indicator indicates that cleaning has been successfully performed. If, however, cracks and/or contaminate residue exist in the container, the surface irregularities presented thereby collect the indicator and continually release it throughout the duration of the post-rinse phase. Therefore, the indicator will be detected in the post-rinse fluid even at the end of the post-rinse phase. Indicator detection, thus, indicates the presence of undesirable contaminates within the container.

An alternative embodiment entails testing the post-rinse fluid for the presence of adenosine triphosphate whether or not a contaminate indicator has been introduced into the container.

DESCRIPTION OF THE PREFERRED EMBODIMENTS

In accordance with a first preferred embodiment of the present invention, there is provided a method of cleaning reusable containers which incorporates prior methods of cleaning such containers. In particular, this preferred embodiment includes the steps of emptying product residues from the container, pre-rinsing the container with a fluid such as water, cleaning the container with cleaning chemicals, post-rinsing the container with a fluid such as water, and then steam sterilizing the container. Additionally, however, the present invention also entails introducing a contaminate indicator into the container to be cleaned either at the beginning of the cleaning process or shortly thereafter, i.e., prior to the chemical cleaning step.

Preferably, the indicator is introduced into the container by mixing the indicator with a carrier liquid to form a highly concentrated mixture and, then, rinsing the container with such mixture. Preferably, the indicator is a living organism, e.g., a bacterium, which can be detected in the presence of ultra-violet (UV) light. Such organisms are especially preferred because they cause easily detectable UV-light reactions when subjected to UV-light. Such organisms also offer the advantage of not being injurious to humans. In particular, if the container is to be refilled with a beer product, aerobic bacteria can be used as the indicator since such bacteria cannot damage the refilling beer product should some trace amount of the indicator bacteria remain after the cleaning process. Similarly, other bacteria which are not damaging to a given beverage should be selected when such other beverage is the refilling product. This ensures that, in all cases, the indicator itself will not damage the refilling beverage.

When the indicator is introduced prior to the pre-rinse phase of the cleaning process, it will lodge in the beverage residue, which will certainly be present, and any deposits which may exist in the container. The conventional cleaning process can then be performed on the container in an attempt to remove all of the contaminates along with the indicator. However, the post-rinsing fluid of the post-rinsing step is monitored to determine whether any of the indicator is present in the outflowing post-rinse fluid and, if so, in what concentration. This monitoring can be performed using a UV light detector, a non-UV light detector, a field-counting device, or one of the known substitutes therefor, which is located within the output piping of the cleaning apparatus. The use of detectors such as these is especially preferred because they are capable of sensing the presence of the indicator in a matter of seconds. Thus, detection of an insufficiently clean container can occur long prior to container refilling and, hence, product waste can be avoided. If no cracks or contaminate deposits are present, the indicator, along with loose dirt particles, will be flushed out of the container during the chemical cleaning phase or early in the post-rinse phase of the cleaning process. Thus, if the indicator is detected throughout the end of the post-rinse phase, the container is clearly not sufficiently clean. In such a case, the detector generates an appropriate control signal indicating that the container should be removed from the production line and electronically marked with the reason for the rejection. This removal and marking can then be automatically performed by a control system of the cleaning apparatus. Finally, if the container is not rejected, the container is steam-sterilized as an additional prophylactic measure. This will kill any bacteria which may have escaped detection and may remain in the container. This, in turn, ensures that such residual bacteria cannot have a deleterious effect on the refilling product or the ultimate consumer.

In a modified form of the method described above, the control system can be configured to generate a container rejecting control signal if the concentration of the indicator in the post-rinse fluid is above a pre-determined threshold level. Such an arrangement allows a container possessing trace amounts of the indicator to continue down the production line for refilling, while rejecting only those containers possessing an intolerably high level of contaminates.

In a second preferred embodiment, the contaminate indicator is not introduced into the container until after chemical cleaning has occurred. This method embodiment is especially preferred when an indicator is selected which can be adversely affected by either the chemicals or temperatures used during the step of chemical cleaning. In particular, this embodiment is recommended if chemical cleaning could affect the indicator in such a way that it cannot be recognized by the detector during post-rinsing. For example, if the selected indicator would be chemically changed due to exposure to the cleaning chemicals, the indicator should be introduced after the chemical cleaning phase. Similarly, if the properties of the indicator are changed by the high temperatures normally present during the chemical cleaning phase (e.g., at least about 85° Celsius) the indicator should be introduced after the chemical cleaning phase. To help preserve the integrity of the indicator, the container should be briefly rinsed with water to reduce the chemical concentration and/or the temperature in the container after chemical cleaning, but prior to introduction of the indicator. Once this brief rinsing has occurred, the indicator can be introduced into the container using a carrier liquid as described above with respect to the first preferred embodiment. Then, the process will continue as described above and the container will either be accepted for refilling or rejected and removed from the production line.

According to yet another preferred embodiment of the present invention, the post-rinse liquid is monitored for the presence, and/or the concentration, of adenosine triphosphate (ATP). This embodiment is otherwise substantially similar to the first preferred embodiment described above.

For example, container rejection or acceptance occurs based on the results of the step of testing for the indicator. Since ATP is present in all organisms, it will be present in the post-rinse fluid if contaminating bacteria are present in the container whether or not an indicator organism has been introduced into the container. Because ATP is present in particles produced by all organisms, ATP measurement provides an unambiguous indication of the presence of organic contaminants and of any bacterial indicator which has been added during cleaning. ATP analysis, however, presently takes approximately two minutes. This is far longer than the five to twenty second post-rinse time normally employed in typical cleaning processes. Nonetheless, this analysis time is negligible compared to the several days of incubation and analysis previously necessary to detect contaminated containers.

While the present invention has been described in connection with what is presently considered to be the most practical and preferred embodiments, it is to be understood that the invention is not limited to the disclosed embodiments, but is intended to cover all of the various modifications and equivalent arrangements within the scope and spirit of the appended claims.

What is claimed is:

1. A method of cleaning a container comprising the steps of:
   pre-rinsing the container with a pre-rinse fluid whereby the pre-rinse fluid is introduced into and removed from the container;
   chemically cleaning the container whereby a cleaning chemical is introduced into and removed from the container;
   post-rinsing the container with a post-rinse fluid whereby the post-rinse fluid is introduced into and removed from the container;
   introducing a contaminate indicator into the container prior to said step of post-rinsing, wherein said contaminate indicator comprises living organisms; and
   testing the post-rinse fluid for the presence of the contaminate indicator during at least a portion of said step of post-rinsing.

2. A method as recited in claim 1, wherein said step of introducing a contaminate indicator comprises introducing aerobic bacteria into the container prior to said step of post-rinsing.

3. A method as recited in claim 1, wherein said step of introducing a contaminate indicator comprises introducing bacteria which are detectable when subjected to ultra-violet light into the container prior to said step of post-rinsing.

4. A method of cleaning a container comprising the steps of:
   pre-rinsing the container with a pre-rinse fluid whereby the pre-rinse fluid is introduced into and removed from the container;
   chemically cleaning the container whereby a cleaning chemical is introduced into and removed from the container;
   post-rinsing the container with a post-rinse fluid whereby the post-rinse fluid is introduced into and removed from the container;
   introducing a contaminate indicator into the container prior to said step of post-rinsing, wherein said contaminate indicator comprises adenosine triphosphate; and
   testing the post-rinse fluid for the presence of the contaminate indicator during at least a portion of said step of post-rinsing.

5. A method of cleaning a container comprising the steps of:
   pre-rinsing the container with a pre-rinse fluid whereby the pre-rinse fluid is introduced into and removed from the container;
   chemically cleaning the container whereby a cleaning chemical is introduced into and removed from the container;
   post-rinsing the container with a post-rinse fluid whereby the post-rinse fluid is introduced into and removed from the container;
   introducing a contaminate indicator into the container prior to said step of post-rinsing;
   testing the post-rinse fluid for the presence of the contaminate indicator during at least a portion of said step of post-rinsing; and
   sterilizing the container after said step of post-rinsing occurs.

6. A method of cleaning a container comprising the steps of:
   pre-rinsing the container with a pre-rinse fluid whereby the pre-rinse fluid is introduced into and removed from the container;
   chemically cleaning the container whereby a cleaning chemical is introduced into and removed from the container;
   post-rinsing the container with a post-rinse fluid whereby the post-rinse fluid is introduced into and removed from the container;
   introducing a contaminate indicator into the container prior to said step of post-rinsing;
   testing the post-rinse fluid for the presence of the contaminate indicator during at least a portion of said step of post-rinsing;
   wherein said contaminate indicator has contaminate indicating characteristics which can be impaired; and
   wherein said contaminate indicator is introduced into said container subsequent to a step of said method which will impair the contaminate indicating characteristics of the contaminate indicator.

7. A method of cleaning a container comprising the steps of:
   pre-rinsing the container with a pre-rinse fluid whereby the pre-rinse fluid is introduced into and removed from the container;
   chemically cleaning the container whereby a cleaning chemical is introduced into and removed from the container;
   post-rinsing the container with a post-rinse fluid whereby the post-rinse fluid is introduced into and removed from the container;
   introducing a contaminate indicator into the container prior to said step of post-rinsing, wherein said contaminate indicator comprises aerobic bacteria; and
   testing the post-rinse fluid for the presence of the contaminate indicator during at least a portion of said step of post-rinsing.

8. A method of cleaning a container comprising the steps of:
   pre-rinsing the container with a pre-rinse fluid whereby the pre-rinse fluid is introduced into and removed from the container;
   chemically cleaning the container whereby a cleaning chemical is introduced into and removed from the container;

post-rinsing the container with a post-rinse fluid whereby the post-rinse fluid is introduced into and removed from the container;

introducing a contaminate indicator into the container prior to said step of post-rinsing, wherein said contaminate indicator comprises bacteria which are detectable when subjected to ultra-violet light; and testing the post-rinse fluid for the presence of the contaminate indicator during at least a portion of said step of post-rinsing.

9. A method of cleaning a container comprising the steps of:

pre-rinsing the container with a pre-rinse fluid whereby the pre-rinse fluid is introduced into and removed from the container;

chemically cleaning the container whereby a cleaning chemical is introduced into and removed from the container;

post-rinsing the container with a post-rinse fluid whereby the post-rinse fluid is introduced into and removed from the container;

testing the post-rinse fluid for the presence of adenosine triphosphate during at least a portion of said step of post rinsing.

10. A method of cleaning a container comprising the steps of:

pre-rinsing the container with a pre-rinse fluid whereby the pre-rinse fluid is introduced into and removed from the container;

chemically cleaning the container whereby a cleaning chemical is introduced into and removed from the container;

post-rinsing the container with a post-rinse fluid whereby the post-rinse fluid is introduced into and removed from the container;

introducing a contaminate indicator into the container prior to said step of post-rinsing, wherein said contaminate indicator comprises adenosine triphosphate;

testing the post-rinse fluid for the presence of the contaminate indicator during at least a portion of said step of post-rinsing; and sterilizing the container after said step of post-rinsing occurs.

* * * * *

UNITED STATES PATENT AND TRADEMARK OFFICE
CERTIFICATE OF CORRECTION

PATENT NO.        : 5,833,763
APPLICATION NO. : 08/716057
DATED              : November 10, 1998
INVENTOR(S)       : Till It is certified that error appears in the above-identified patent and that said Letters Patent is hereby corrected as shown below:

Column 6:

Line 13, after "post-rinsing" insert

--, wherein said contaminate indicator comprises living organisms--.

Signed and Sealed this

First Day of July, 2008

JON W. DUDAS
*Director of the United States Patent and Trademark Office*